United States Patent [19]
Stevens et al.

[11] Patent Number: 5,817,509
[45] Date of Patent: *Oct. 6, 1998

[54] CULTURE VESSEL ASSEMBLY

[75] Inventors: Timothy A. Stevens, Warwick, N.Y.;
Tadeusz A. Tyndorf, Manalapan;
Susan L. Barker, Tenafly, both of N.J.

[73] Assignee: Becton Dickinson and Company, Franklin Lakes, N.J.

[ * ] Notice: The term of this patent shall not extend beyond the expiration date of Pat. No. 5,780,294.

[21] Appl. No.: 818,648

[22] Filed: Mar. 19, 1997

[51] Int. Cl.$^6$ ..................................................... C12M 3/00
[52] U.S. Cl. .................................... 435/297.5; 435/305.3; 435/305.4
[58] Field of Search ............................. 435/288.3, 288.4, 435/297.5, 305.1, 305.2, 305.3, 305.4; 422/102

[56] References Cited

U.S. PATENT DOCUMENTS

4,657,867  4/1987  Guhl et al. ............................. 435/284
5,358,871  10/1994  Stevens et al. .......................... 435/284
5,571,721  11/1996  Turner .................................. 435/305.1
5,605,813  2/1997  Stevens et al. ....................... 435/40.52

*Primary Examiner*—David Redding
*Attorney, Agent, or Firm*—Nanette S. Thomas; Bruce S. Weintraub

[57] ABSTRACT

A multiwell tissue culture assembly for culturing cells comprising a plate and a lid. The plate includes a plurality of wells for receiving liquids therein and the lid includes means for varying the gas diffusion into and out of the assembly and for substantially minimizing biological contamination of the cells being cultured. The means for varying the gas diffusion is a gas permeable membrane provided in an opening in the lid and a removable thin impermeable film label is provided for selectively occluding passage of gases through the gas permeable membrane. The means for minimizing biological contamination of the cells being cultured is a sealing material located in the lid and means for removably securing the lid and the plate together whereby the sealing material is compressed between the lid and the plate.

27 Claims, 9 Drawing Sheets

CULTURE VESSEL ASSEMBLY

BACKGROUND OF THE INVENTION

1. Field of the Invention

This invention relates to an apparatus and procedures for growing cells or tissue culture in vitro and more particularly to a culture vessel assembly having means for varying the gas diffusion rate into and out of the assembly and for substantially minimizing biological contamination of the cells or tissue culture in the assembly.

2. Description of Related Art

Culture vessels are described in U.S. Pat. Nos. 4,495,289, 5,026,649, 5,358,871 and 5,366,893 and European Patent Application No. 0 483 620 A2 and U.K. Patent Application No. GB 2 268 187 A. Culture vessels comprise wells which generally have a circular shape and size which permits the introduction therein of a cell culture insert having a membrane upon which cell attachment, growth and differentiation occur. The culture vessels containing the wells are typically rectangular and have a standard size in order to accommodate standard analytical apparatus. Cell culture inserts used in culture vessels are described in U.S. Pat. Nos. 4,871,674, 5,026,649 and 5,366,893 and are herein incorporated by reference.

The culture of cells is dependent upon the ability to supply sufficient oxygen to the cells without causing cellular damage. The supply of oxygen for cell respiration is from the atmosphere in the header space above the cells via the liquid culture medium.

Aeration of the culture, by for example, sparging, surface aeration, medium perfusion, can increase the oxygen availability, however such methods can cause cellular damage. Silicone rubber tubing has been used to improve gas exchange in cell culture, by running the tubing between the well and the atmosphere, but this method is inconvenient and may cause contamination to the cell suspension.

Although there are a number of culture vessels commercially available and described in patent publications, it is believed that there are no culture vessels available that provide a means for varying the gas diffusion rate into and out of a culture vessel assembly while still providing a closed system whereby entry or exit of biological contaminants into or out of the vessel is substantially minimized.

SUMMARY OF THE INVENTION

The present invention is an assembly for growing cells or tissue culture in vitro. The assembly comprises a test plate with wells shaped to accommodate an insert, such as a cell culture insert, or for receiving tissue culture media and a removable lid.

The test plate preferably comprises an upper surface, a lower surface, and a plurality of wells. Each well is substantially disposed between the upper and lower surface of the test plate.

The assembly further includes a removable lid which can be positioned over the upper surface of the test plate. The lid includes a top wall and a peripheral skirt that extends downwardly from the top wall. Inside the lid, along the inside perimeter of the skirt, where the skirt and the top wall meet, is a sealing material such as silicon. The lid serves to prevent the loss of sample from the well interior, to protect the contents of the assembly from the environment and to protect the user from the contents of the assembly should it contain a harmful or potentially harmful material.

In addition, the assembly further comprises means for removably securing the lid and the plate together whereby the sealing material is compressed between the lid and plate interface and the inside of the assembly is substantially protected from the outside environment thereby providing a biologically secure environment in the assembly.

Therefore, the assembly wherein the lid and the plate are securely arranged together serves to prevent the loss of sample from the well interior, protects the contents of the assembly from the environment, protects the contents of the assembly from cross-contamination between the wells and protects the user from the contents of the assembly should it contain a harmful or potentially harmful material.

Preferably, the means for removably securing the lid and plate is a lever on the lid and a receiving handle on the plate. Most preferably, the receiving handle is a frame surrounding an open area wherein the lever fits into the open area and connects with the frame. When the lid and plate are being placed together, a downwardly force is applied to the lever along the horizontal axis as the lid is being lowered in place over the upper surface of the plate. The compressed lever is placed into the open area of the receiving handle and then as the force is released from the lever, the lever will snap-fit with the frame of the receiving handle.

The action of snap-fitting the lever with the receiving handle may cause an audible-snap and in turn provides a non-permanent lock. In addition, the lever and receiving handle when brought together, substantially seals the lid and the plate together whereby the sealing material on the lid is compressed in the lid and plate interface. The compressed sealing material thereby substantially eliminates the exchange of liquid and/or gases between the lid and plate interface.

The lid is removed from the plate by applying a force to the level along the horizontal axis, to cause the lever to unsecure from the receiving handle while lifting the lid from the plate.

The plate and related removable lid may be formed in different sizes and geometric configurations so as to be used with different size and geometric configured cell culture inserts. The removable lid may be formed to be positioned over the upper surface of the plate in one orientation so as to reduce cross contamination between the wells in the event the lid is repositioned over the upper surface of the plate. The plate and the removable lid are preferably made of an optically clear plastic to facilitate viewing of the wells and cell culture inserts.

Preferably, the lid further comprises means for allowing gas diffusion into and out of the wells of the plate. Most preferably, the means for allowing the gas diffusion into and out of the wells of the plate is at least one port. Associated with the port is a gas permeable membrane. Most preferably, the gas permeable membrane is liquid impermeable.

Further associated with the lid is a means for selectively occluding the gas permeable membrane without removing the lid from the test plate. Preferably, the means for selectively occluding the membrane is a thin impermeable film. A thin film may be removably attached to the top of the lid over the port to restrict exposure of the gas permeable membrane to the atmosphere. The thin impermeable film assists is maintaining the biological security of the environment in the wells because the lid does not have to be lifted or removed from the test plate.

Most preferably, the means for selectively occluding the membrane is a peel-away gas impermeable label. Most preferably, the label is plastic. Preferred materials of the label, include but are not limited to polymeric substrate resins that are impermeable to gases and liquids. The label may be transparent or color coded. Moreover, the surface of the label may be such that additional information may be hand written on the label.

Although it is within the purview of the invention to provide a label that is circular, labels of different geometric configurations may be provided.

The label allows the user to control the exchange of gas in the wells so that the desired growth of the cell culture can be facilitated while still providing a closed system that substantially prevents entry of microbial organisms or other contaminants into the wells of the test plate. The label substantially maximizes gas exchange while minimizing the possibility of contamination in the wells of the test plate.

The label does not compromise sterility or invite leakage into the test plate. Other advantages is that the label is reusable and is economically feasible to manufacture.

A notable advantage of the port and gas permeable membrane is that gas exchange takes place exclusively through the membrane without having to partially open the lid and therefore the sterility and leakage into the wells is substantially minimized.

Most notably, the assembly of the present invention provides the following advantages: (1) a closed vented environment while maintaining sterility and controlling gas exchange; (2) containment of potentially hazardous samples; (3) minimizing contamination of specimen in the assembly with environmental/exogenous contaminants such as yeast, bacteria and/or virus; and (4) a biologically secure environment.

In addition, the assembly of the present invention is particularly advantageous when culturing layers of cells, such as in skin cultures where it is desirable to produce layers of keratinocytes for skin grafting in a sterile and gas exchange controlled environment.

In addition, the present invention allows for the controlled passage of oxygen directly to the dividing cells which lie on the membrane surface of the cell insert.

In accordance with the principles of the assembly of the present invention, significant improvements over currently known and available multiwell tissue culture assemblies are provided. Most importantly, the assembly of the present invention substantially improves gas diffusion into and out of the assembly while maintaining the sterility of the contents of the multiwell plate and allows adequate gaseous exchange to occur between the wells and the external environment. Accordingly, the assembly of the present invention provides a biologically secure closed environment so as to optimize conditions for cell culturing procedures whereby entry or exit of biological contaminants, gases and/or liquids is substantially minimized.

DETAILED DESCRIPTION

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 1:
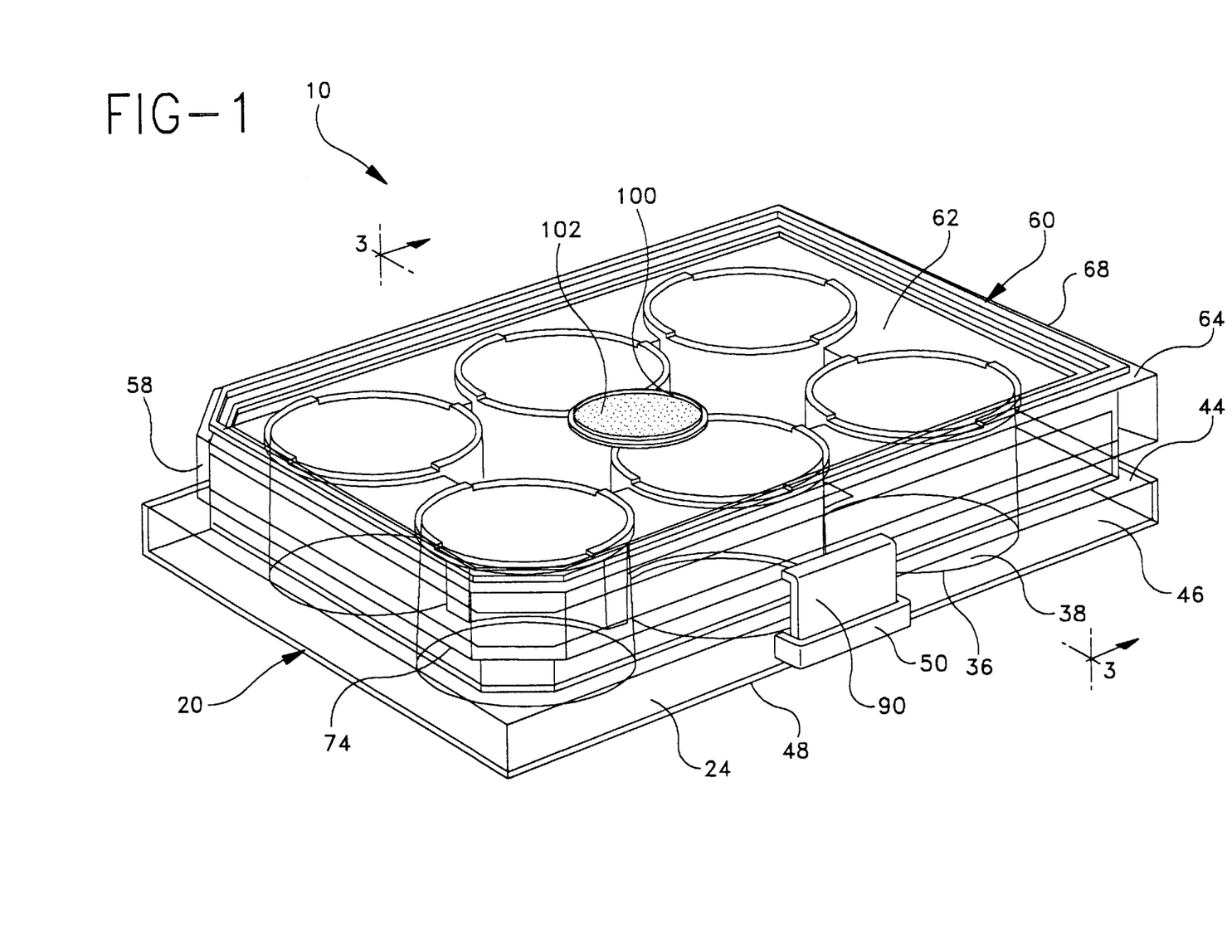
FIG. 1 is a perspective view of the assembly of the present invention.
Figure 2:
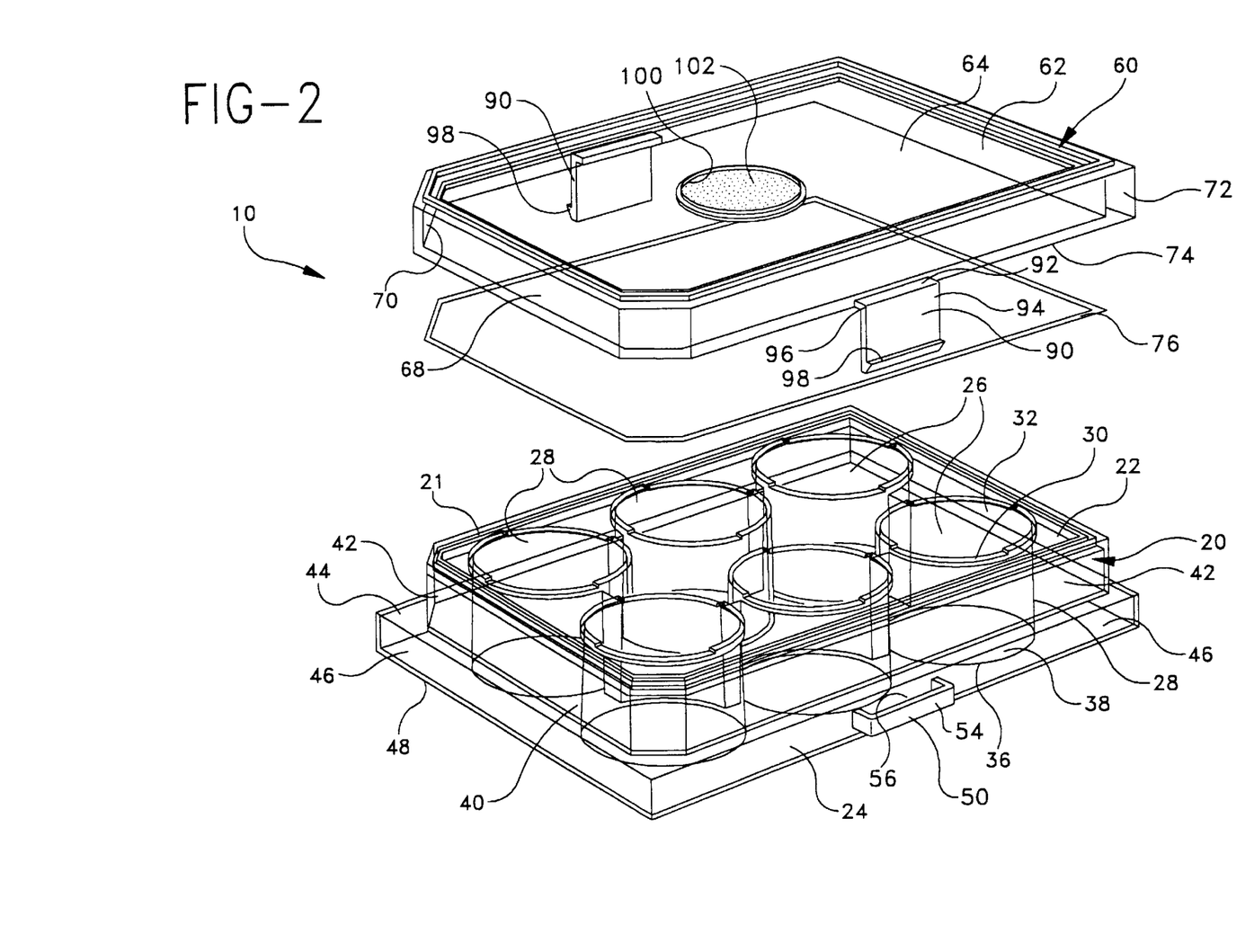
FIG. 2 is a perspective view of the assembly of the present invention with the lid removed.

An apparatus 10 for growing tissue culture as shown in FIGS. 1–2 includes a culture vessel plate 20 and a lid 60. As shown in FIGS. 1–2, culture vessel plate 20 includes an upper surface 22 and lower surface 24. The culture vessel plate further includes a number of wells 26 each comprising a sidewall 28 extending from upper surface 22 of the plate to lower surface 24 of the plate. Each well comprises a top portion 30 and a bottom portion 36. Top portion 30 comprises an open end 32 that extends to a bottom portion 36 that comprises a closed end 38.

There may be any number of wells 26 in plate 20, although six, twelve, twenty-four, forty-eight and ninety-six well plates are commonly known and available. In FIG. 1, a six-well plate is illustrated, merely for exemplary purposes. Most standard multiwell plates have the wells arranged in orthogonal rows and columns so as to be able to clearly identify the individual wells being used, of course, the arrangement of the wells in plate 20 is not an essential limitation of the present invention, since any arrangement of wells is contemplated by the invention.

Plate 20, as illustrated in the figures, typically is transparent and may be molded, for example, of polyvinylchloride or polystyrene.

Surrounding the wells and forming the outside border of plate 20 is sidewall 40. In the present embodiment, plate 20 has six (6) sidewalls. Well known tissue culture plates are rectangle or quadrilaterally shaped, although for purposes of the present invention the plate may be fabricated in any practical configuration and contain any number of wells.

Figure 3:
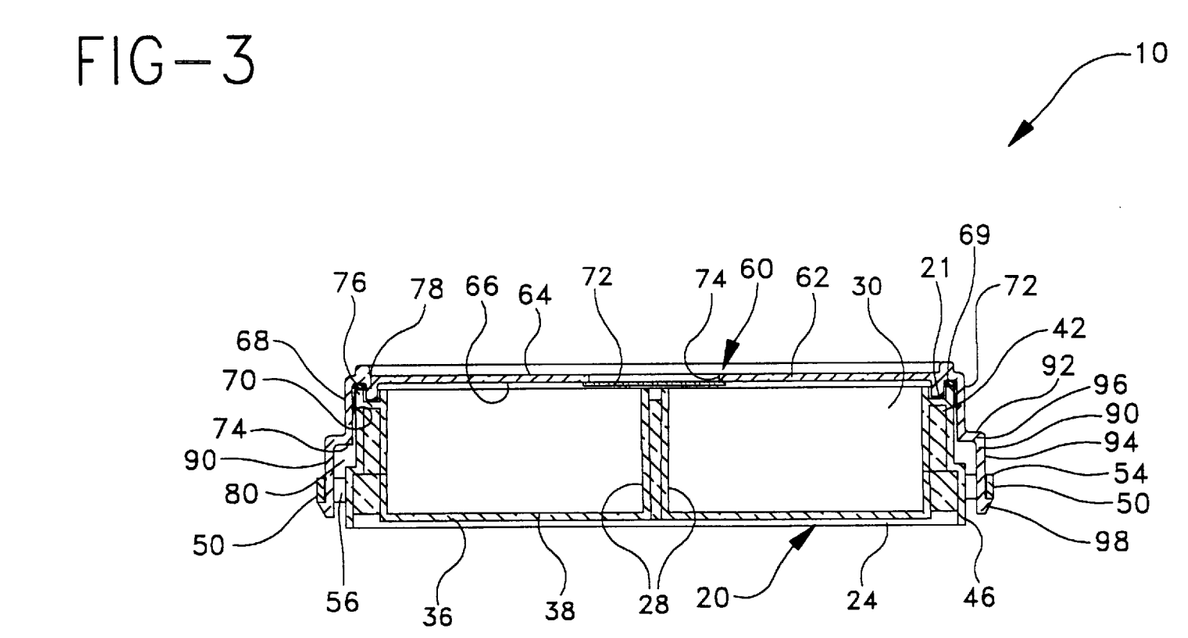
FIG. 3 is a cross-sectional view of the assembly taken along 3—3 of FIG. 1.
Figure 4:
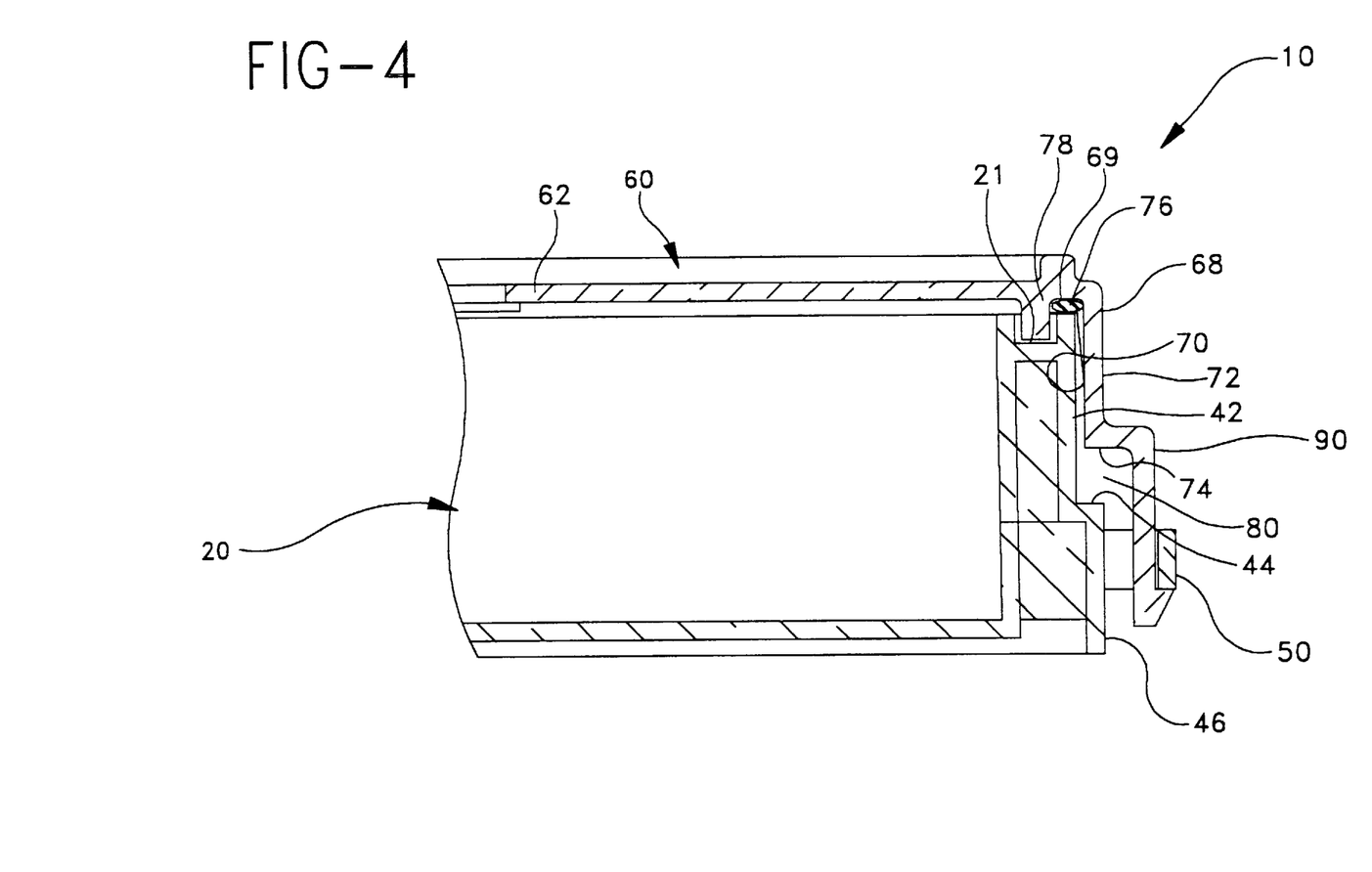
FIG. 4 is an enlarged, partial sectional view of the assembly of FIG. 3.

Spaced inwardly from sidewall 40 of the plate and around the upper surface of plate 20 is a recessed ledge 21 as more clearly seen in FIGS. 3 and 4, taken in conjunction with FIGS. 1 and 2. Ledge 21 forms a border around the wells on the upper surface 22 of plate 20 and wherein the sidewall 40 extend to a position raised above the ledge thereby forming a rim surrounding the ledge.

Sidewall 40 comprises a two-step section comprising an upper section 42 and a lower section 46. Lower section 46 is stepped from upper section 42 by an annular shoulder 44 between the upper and lower sections. Therefore, upper section 42 extends from upper surface 22 to annular shoulder 44 and lower section 46 extends from annular shoulder 44 to a bottom surface 48 of lower surface 24.

Lower section 46 serves as an annular base for plate 20 when the present multiwell tissue culture apparatus is being used.

As shown in FIGS. 1–3, handles 50 are attached on opposite sides of lower section 46 of plate 20. Each handle 50 extends outwardly from lower section 46 of plate 20. Each handle has a closed frame 54 that surrounds an opened area 56. It is well within the purview of this invention that the handle may comprise two separate pieces and be of any particular geometric configuration.

Lid 60 is a separate, removable member which covers all of the wells of the plate. Although lid 60 is illustrated in all of the figures, the details of lid 60 are best illustrated in FIGS. 2–4. Lid 60 includes a substantially planar cover 62 large enough to extend over all of the wells of the plate. Planar cover 62 has a top surface 64 and a bottom surface 66. The shape of cover 62 is compatible with the shape of plate 20. Most preferably, as shown in FIG. 1, lid 60 is formed to be positioned over the upper surface of the plate in one orientation so as to reduce cross contamination between the wells in the event the user tries to reposition the lid over the plate.

Extending around cover 62 is a downwardly depending skirt 68 which forms a border around lid 60. Skirt 68 has an inner wall surface 70 and an outer wall surface 72, and six sides each of which extends downwardly from the cover to a bottom stop surface 74. As shown in FIG. 4, the transition between cover 62 and depending skirt 68 is a perimeter area 69. In addition, along inner perimeter area 69 is a sealing material 76 such as silicon. Inwardly, spaced from skirt 68 and extending downwardly from bottom surface 66 of the planar cover is rib 78. This rib, lying substantially parallel to inner wall surface 70 of skirt 68, is positioned on the cover so as to depend downwardly into recessed ledge 21 in the plate.

As shown in FIGS. 1–4, located on cover 62 is an orifice or port 100 and a gas permeable, liquid impermeable membrane 102 is associated with the orifice. Gas permeable membrane materials may be made from any suitable gas permeable material so long as it provides free passage of gases such as oxygen and carbon dioxide into the test plate while preventing microorganisms such as bacteria and fungi from passing there through. These materials include polyethylene, polycarbonate, acrylic co-polymers and polytetrafluoroethylene.

As shown in FIG. 3, when lid 60 is positioned over plate 20, skirt 68 extends towards annular shoulder 44 of the multiwell plate thereby leaving a space 80 therebetween annular shoulder 44 and bottom stop surface 74. As shown in FIGS. 3 and 4, sealing material 76 is compressed between the perimeter area 69 and sidewall 40 of the plate to substantially close off any leakage into and/or out of the environment.

As shown in FIGS. 1–2, levers 90 are attached on opposite sides of the outer wall surface 72 of skirt 68. Each lever extends from outer wall surface 72 of skirt 68. It is well within the purview of the invention that the levers may be of any particular configuration so long as they may easily cooperate with handles 50 of the plate. As shown in FIGS. 3–4, each lever 90 has a step configuration comprising a rearward end 92 that extends outwardly from outer wall surface 72 and a forward or working end 94. Rearward end 92 and forward end 94 meet at a pivot position 96. The pivot position provides flexibility to the forward end so that it may be pushed or compressed towards the outer wall surface of the skirt. At forward end 94 is a cleat 98 that extends outwardly from the forward end and is used to secure the lever with the handle whereby the cleat mates with the frame of the handle.

Figure 5:
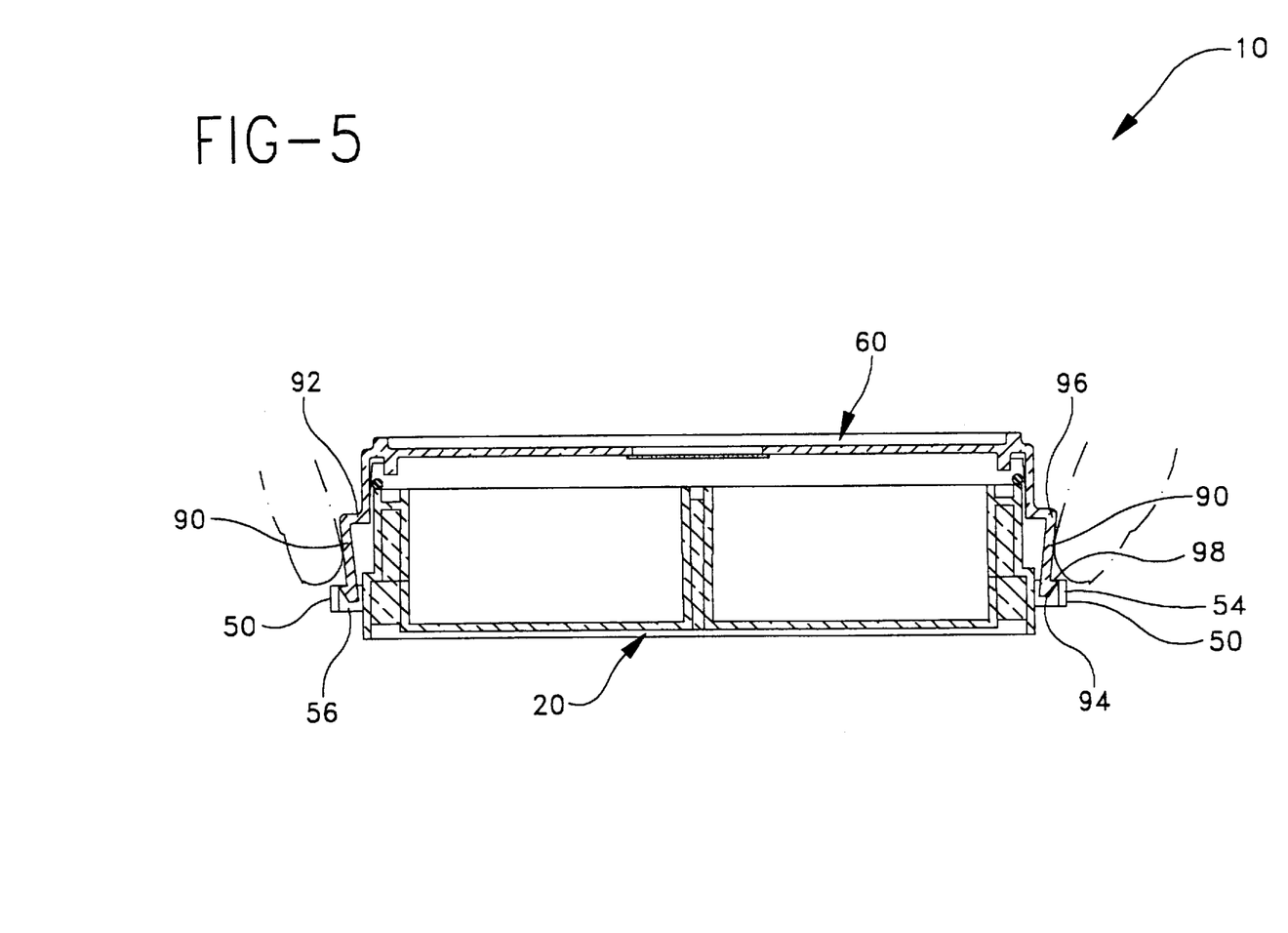
FIG. 5 illustrates the placement of the lid on the plate.

In use, as shown in FIG. 5, a horizontal force is applied to each lever at the forward end with the thumb and forefinger of the user's hand, thereby causing each forward end of the lever to compress towards the outer wall surface of the skirt. Then as the lid is lowered over the top of the plate, and the levers are slide into the open areas of the handles, the force to each lever is removed and the cleat of each lever snap-fits with the frame of the handle. The snap-fit of the levers may cause an audible-snap. The snap-fit causes a non-permanent lock between the lid and plate and causes the sealing material 76 to be compressed between perimeter area 69 of the lid and sidewall 40 of the plate.

Figure 6:
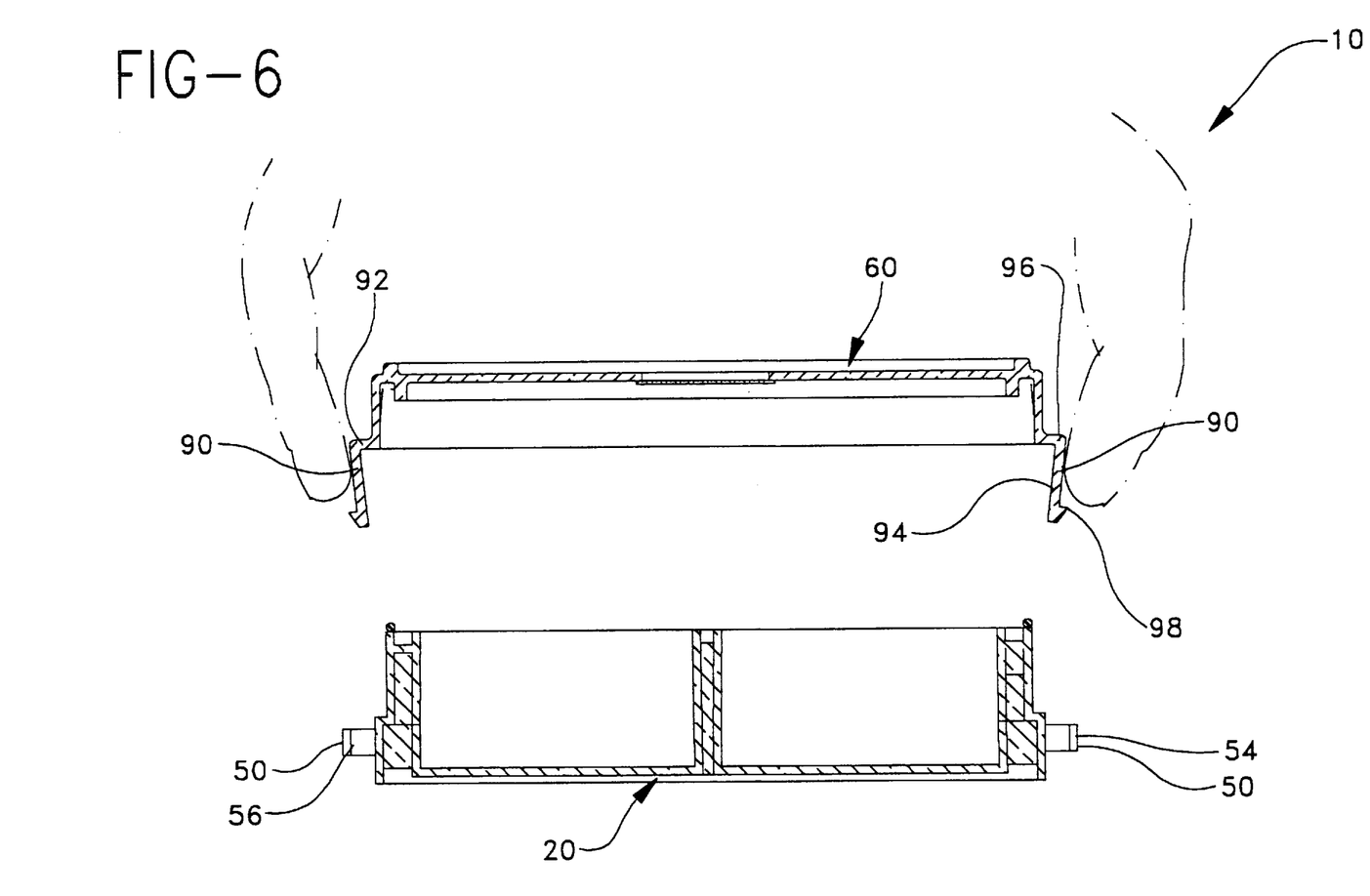
FIG. 6 illustrates the removal of the lid from the plate.

As shown in FIG. 6, the lid is removed from the plate whereby the thumb and forefinger of the user's hand applies a horizontal force to the forward ends of the levers towards the outerwall surfaces of the skirt so that the cleat of each lever releases from the handle frame and then an upward, lifting movement by the user brings the lid away from the plate.

Figure 7:
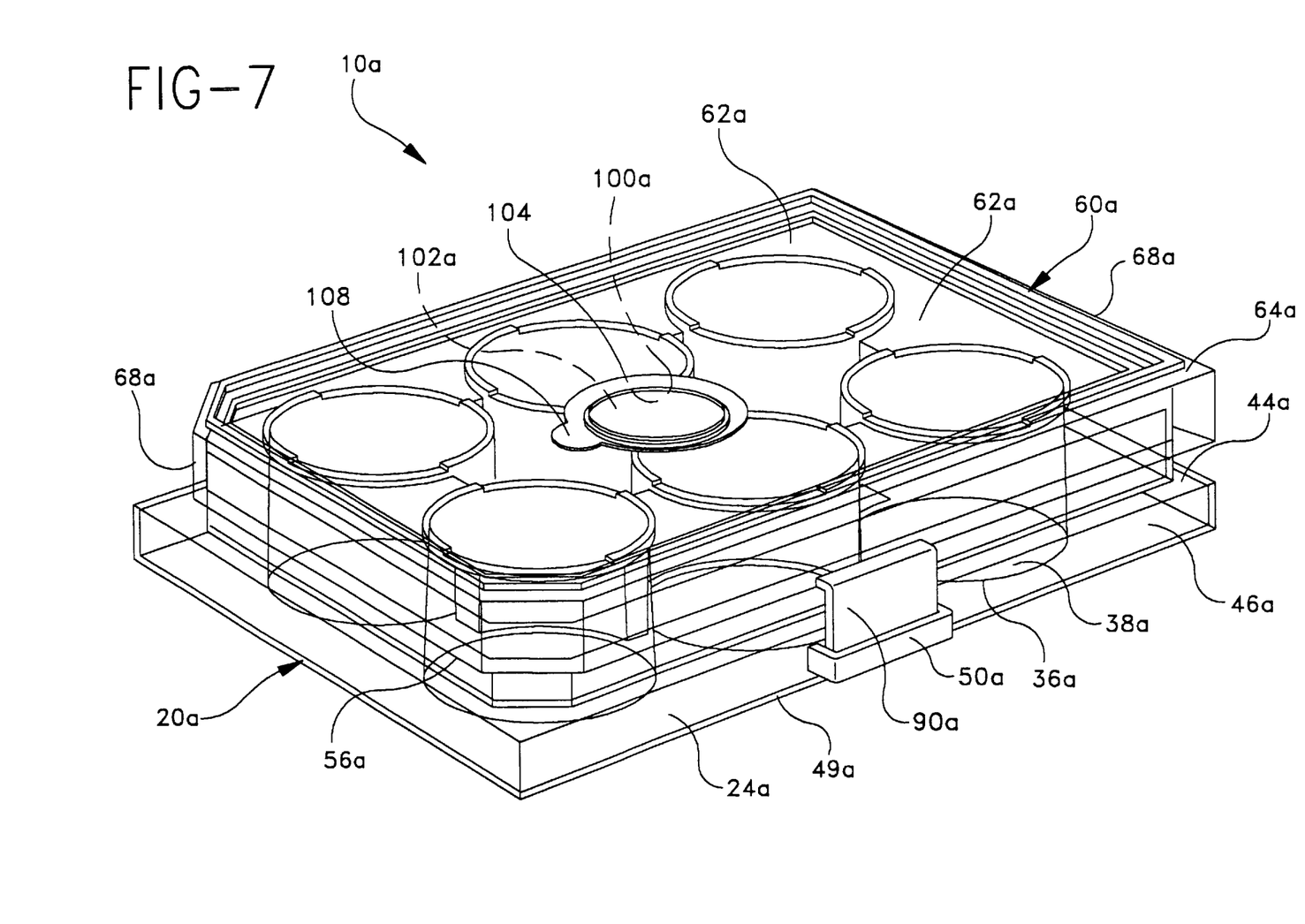
FIG. 7 is a perspective view of an alternate embodiment of the present invention with a label on the lid covering the orifice.

An additional embodiment of the invention as shown in FIG. 7 includes many components which are substantially identical to the components of FIG. 1. Accordingly, similar components performing similar functions will be numbered identically to those components of FIG. 1 except that a suffix "a" will be used to identify those similar components in FIG. 7.

As shown in FIG. 7, optionally a peel-away thin film label 104 is removably attached to cover 62a to selectively occlude the membrane 102a of orifice 100a. The film may be fully or partially removed or left in place according to the particular culture requirements.

Conventional means are used to apply the peel-away thin film label to the cover. These means include adhesive materials such as pressure sensitive materials, wherein the thin film label can be easily partially or fully removed from the cover as is required and reapplied as needed. The thin film label material may be made of polyethylene or polyethylene terephthalate and the adhesive materials may include acrylic adhesives.

As shown in FIG. 7, optional peel-away thin film label 104 is circular and has a tab 108 for ease of use. Although it is within the purview of the invention to provide a peel-away thin film that is circular, films of different geometries and dimensions may be provided.

Figure 8:
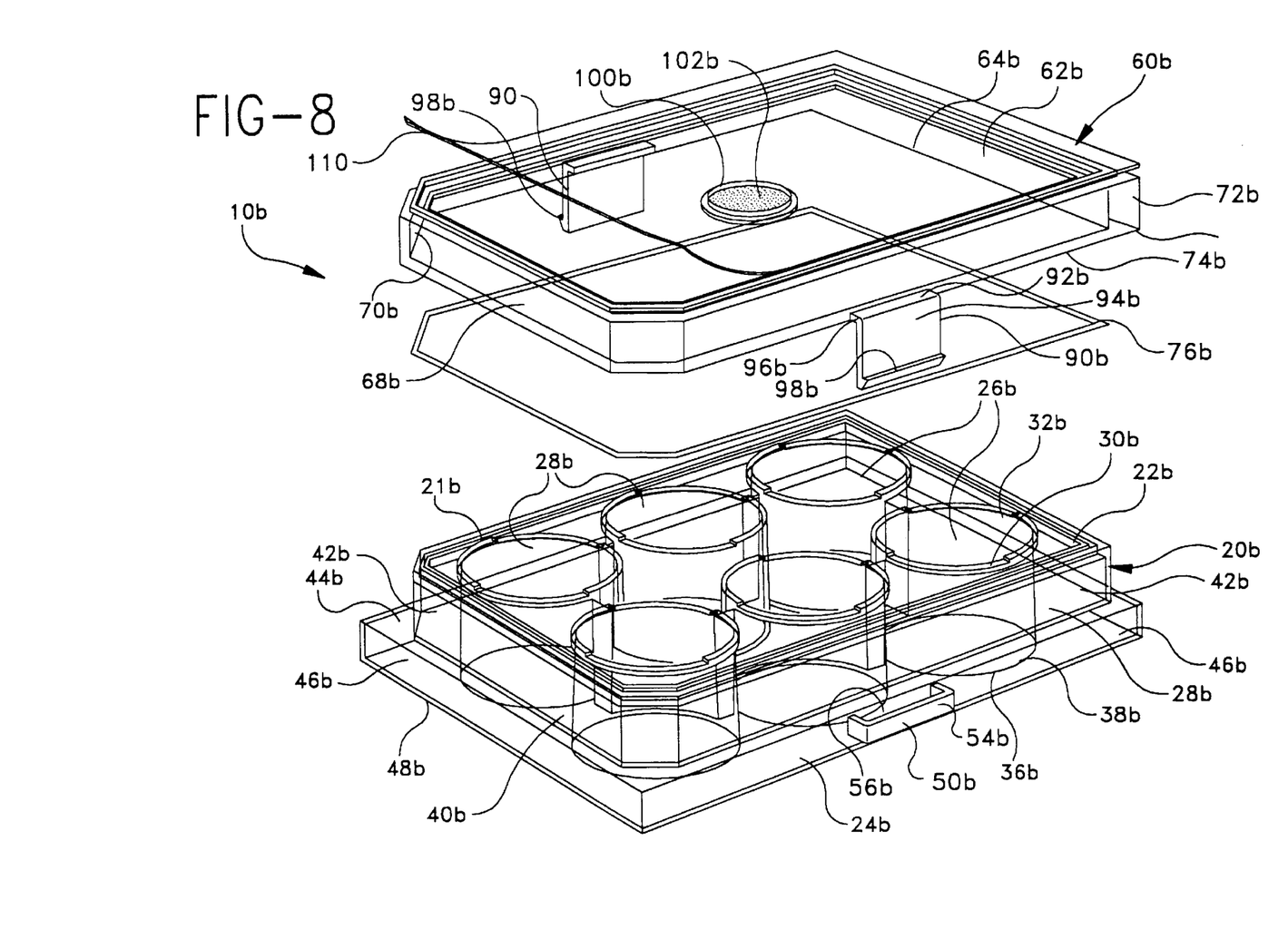
FIG. 8 is a perspective view of an alternate embodiment of the present invention with a label covering the entire lid.

An additional embodiment of the invention as shown in FIG. 8, includes many components which are substantially identical to the components of FIG. 2. Accordingly, similar components performing similar functions will be numbered identically to those components of FIG. 2, except that a suffix "b" will be used to identify those similar components in FIG. 8.

Label 110 as shown in FIG. 8 is an alternate embodiment of the label that can be used with assembly 10b. The alternate embodiment of the invention as shown in FIG. 8, is that label 110 covers the entire planar cover surface of lid 60b.

Figure 9:
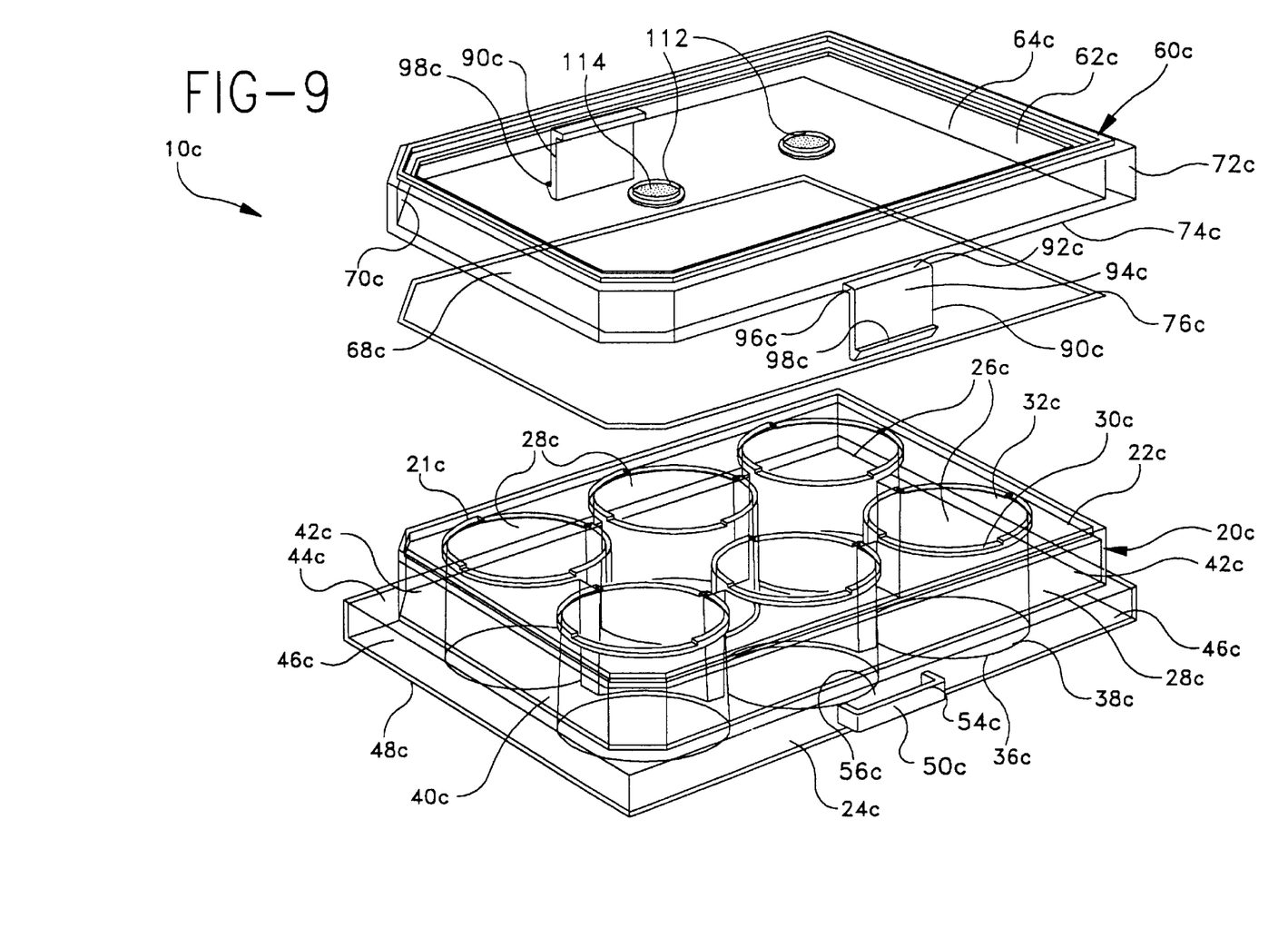
FIG. 9 is a perspective view of an alternate embodiment of the present invention showing more than one orifice in the lid.

An additional embodiment of the invention as shown in FIG. 9 includes many components which are substantially identical to the components of FIG. 2. Accordingly, similar components performing similar functions will be numbered identically to those components of FIG. 2, except that a suffix "c" will be used to identify those similar components in FIG. 9.

Lid 60c as shown in FIG. 9 is an alternate embodiment of the lid that can be used with assembly 10c. The alternate embodiment of the invention as shown in FIG. 9, is that two orifices 112 are located in the planar cover and each has a liquid impermeable membrane 114 associated therewith. Although FIG. 9 only show two orifices, it is well within the purview of the invention to have more than two orifices in the planar cover.

In use, the present invention may be used for culturing cells as follows:

a. removing the lid from the culture vessel assembly by applying a horizontal force to the forward ends of the levers towards the outerwall surface of the skirt so that the cleat of each lever releases from the handle frame and lifting the lid away from the plate;

b. depositing a layer of cells on the membrane of the cell insert within the culture vessel assembly;

c. overlaying the layer of cells with a growth medium;

d. securing the lid over the plate by applying a horizontal force to each lever at the forward end, thereby causing each forward end of the lever to compress towards the outer wall surface of the skirt, lowering the lid over the top of the plate and sliding the levers into the handles on the plate; and e. ventilating the membrane of the cell insert by permitting air access thrusts through the orifice in the lid by removing or partially removing and re-attaching the label over the orifice.

As practitioners-in-the-art will understand, the culture vessel assembly of the present invention may be comprised of simple moldable parts which may be mass produced from a variety of materials, including, for example, polyethylene, polystyrene, polyethylene terephthalate and polypropylene. As will be understood further by practitioners in the art, materials should be selected which provide a small degree of resiliency for the purpose of providing ease of use for subsequent examination of the developed cultured cells.

What is claimed is:

1. An assembly comprising:
   a test plate comprising a plurality of wells having openings therein for receiving tissue culture media or cell culture inserts and upstanding sidewall forming an outside border of said plate;
   a lid removably positioned on said plate over said wells, comprising a substantially planar cover extending over said wells comprising an upper surface and a lower surface, a skirt surrounding said cover defining a plurality of corners on said cover and extending downwardly having an inner and outer surface;
   an inner perimeter area on said lid between said inner surface of said cover and said inner surface of said skirt;
   a sealing material in said perimeter area of said lid;
   means for allowing gas diffusion into and out of said assembly; and
   means for removably securing said lid with said plate.

2. The assembly of claim 1 wherein said means for allowing gases diffusion into and out of said assembly comprises at least one orifice in said cover of said lid comprising a gas permeable membrane.

3. The assembly of claim 2 further comprising a gas impermeable film removably attached to said cover over said orifice and said gas permeable membrane whereby said film may be fully or partially removed to assist in gas diffusion into and out of the assembly.

4. The assembly of claim 1 wherein said sidewall of said plate comprises a two-step section comprising an upper section and a lower section.

5. The assembly of claim 4 wherein said lower section is stepped from said upper section by an annular shoulder.

6. The assembly of claim 5 wherein said skirt of said lid extends to a position adjacent to, but out of contact with, said annular shoulder of said plate.

7. The assembly of claim 1 wherein said wells are arranged in substantially orthogonal rows and columns.

8. The assembly of claim 1 wherein said plate and said lid are made of transparent plastic.

9. The assembly of claim 1 wherein said test plate further comprises a ledge spaced inwardly from said sidewall of said plate and extending around said plate between said sidewall and said wells wherein said sidewall extends to a position raised above said ledge thereby forming a rim surrounding said ledge.

10. The assembly of claim 1 wherein said means for removably securing said lid with said plate is a lever on said outer surface of said skirt and a receiving handle for said lever on said lower section of said sidewall of said plate.

11. The assembly of claim 10 wherein said lever comprises a rearward end extending outwardly from said outer surface of said skirt, a forward end and a pivot position between said rearward end and said forward end.

12. The assembly of claim 11 wherein said lever further comprises a cleat on said forward end.

13. The assembly of claim 10 wherein said receiving handle extends outwardly from said lower section of said plate and comprises a closed frame that surrounds an open area for receiving said lever of said lid.

14. A lid for use in conjunction with a tissue culture plate comprising:
    a substantially planar cover comprising an upper surface and a lower surface;
    a skirt surrounding said cover defining a plurality of corners on said cover and extending downwardly having an inner and outer surface;
    an inner perimeter area in said lid between said upper surface of said cover and said inner surface of said skirt;
    a sealing material in said perimeter area;
    at least one orifice in said cover comprising a gas permeable membrane;
    a gas impermeable film removably attached to said cover over said orifice and said gas permeable membrane whereby said film may be fully or partially removed; and
    a lever on said outer surface of said skirt.

15. The lid of claim 14 wherein said gas impermeable film is a peel-away label.

16. The lid of claim 14 further comprising a plurality of ribs being inwardly spaced from said skirt and extending downwardly from said lower surface of said cover.

17. A device for growing cells or tissue culture in vitro comprising:
    a body comprising an upper surface, a lower surface, a plurality of wells substantially disposed between said upper and lower surface and upstanding sidewall forming an outside border of said body;
    a removable lid, comprising a top wall and a peripheral skirt that extends from said top wall and means for allowing gas diffusion into and out of said device through said top wall, and an inner area in said lid between said top wall and said peripheral skirt, and a sealing material in said inner perimeter area in said lid.

18. The device of claim 17 wherein said means for allowing gas diffusion into and out of the device is at least one orifice and a gas permeable membrane associated with said orifice.

19. The device of claim 18 further comprising a gas impermeable film removably attached to said cover over said orifice, whereby said film may be partially or fully removed to assist with gas diffusion in said device.

20. The device of claim 17 wherein said sidewall of said body comprises a two step section comprising an upper section and a lower section.

21. The device of claim 20 wherein said lower section is stepped from said upper section by said annular shoulder.

22. The device of claim 17 further comprising means for removably securing said lid with said body.

23. The device of claim 22 wherein said means for removably securing said lid with said body is a lever on said peripheral skirt of said lid and a receiving handle for said lever on said sidewall of said body.

24. The assembly of claim 23 wherein said lever comprises a rearward end extending outwardly from said outer surface of said skirt, a forward end and a pivot position between said rearward end and said forward end.

25. The assembly of claim 24 wherein said lever further comprises a cleat on said forward end.

26. The assembly of claim 23 wherein said receiving handle extends outwardly from said lower section of said plate and comprises a closed frame that surrounds an open area for receiving said lever of said lid.

27. A method of culturing cells comprising:
(a) providing a culture vessel comprising a test plate comprising a plurality of wells having openings therein for receiving tissue culture media or a cell culture insert and upstanding sidewall forming an outside border of said plate; at least one cell culture insert positioned in said well of said test plate, a lid removably positioned over said plate comprising a substantially planar cover extending over said wells, a skirt surrounding said cover defining a plurality of corners on said cover and extending downwardly in spaced relation with respect to said sidewall of said plate, an inner perimeter area on said lid between said cover and said skirt; a sealing material in said perimeter area of said lid; an orifice in said planar cover; a gas permeable membrane associated with said orifice; a gas impermeable film removably attached to said cover over said orifice; and means for removably securing said lid with said plate comprising a lever on said skirt of said lid and a receiving handle for said lever on said sidewall of said plate;

(b) removing said lid from said plate by applying a horizontal force to said lever towards said skirt of said lid and sliding said lever from said receiving handle and lifting said lid from said plate;

(c) depositing a layer of cells on the membrane of said cell insert within said culture vessel;

(d) overlaying the layer of cells with a growth medium;

(e) securing said lid over said plate by applying a horizontal force to said lever towards said skirt of said lid and sliding said lever into said receiving handle on said plate; and (f) ventilating said membrane by permitting air access thrusts through said orifice in said lid by partially or fully removing and re-attaching said label over said orifice.

* * * * *